(12) United States Patent
Crisp (10) Patent No.: US 9,952,191 B2
(45) Date of Patent: Apr. 24, 2018

(54) METHOD OF AND/OR APPARATUS FOR MONITORING A CHARACTERISTIC OF A LIQUID SAMPLE

(71) Applicant: Randall Crisp, Tewantin (AU)

(72) Inventor: Randall Crisp, Tewantin (AU)

(73) Assignee: OMA APP IP PTY LTD, Noosaville (QLD) (AU)

( * ) Notice: Subject to any disclaimer, the term of this patent is extended or adjusted under 35 U.S.C. 154(b) by 92 days.

(21) Appl. No.: 14/904,978

(22) PCT Filed: Jul. 13, 2014

(86) PCT No.: PCT/AU2014/050121
§ 371 (c)(1),
(2) Date: Jan. 14, 2016

(87) PCT Pub. No.: WO2015/006821
PCT Pub. Date: Jan. 22, 2015

(65) Prior Publication Data
US 2016/0153950 A1    Jun. 2, 2016

(30) Foreign Application Priority Data

Jul. 16, 2013    (AU) ................................ 2013902640

(51) Int. Cl.
| | |
|---|---|
| *G06K 9/00* | (2006.01) |
| *G01N 33/18* | (2006.01) |
| *G01N 15/06* | (2006.01) |
| *G01N 21/01* | (2006.01) |
| *G01N 21/51* | (2006.01) |
| *C02F 3/00* | (2006.01) |
| *G01N 15/00* | (2006.01) |

(52) U.S. Cl.
CPC ............. *G01N 33/18* (2013.01); *G01N 15/06* (2013.01); *G01N 21/01* (2013.01); *G01N 21/51* (2013.01); *C02F 3/006* (2013.01); *C02F 2209/10* (2013.01); *C02F 2209/11* (2013.01); *G01N 2015/0053* (2013.01); *G01N 2015/0693* (2013.01); *G01N 2201/061* (2013.01)

(58) Field of Classification Search
None
See application file for complete search history.

(56) References Cited

U.S. PATENT DOCUMENTS

| | | | | |
|---|---|---|---|---|
| 2007/0095017 | A1* | 5/2007 | Menke | B65C 9/067 53/167 |
| 2016/0177243 | A1* | 6/2016 | Koretz | A47J 31/4403 261/130 |

FOREIGN PATENT DOCUMENTS

CA    2954779 A1 *    1/2015    ............. G01N 15/06

* cited by examiner

*Primary Examiner* — Delomia L Gilliard
(74) *Attorney, Agent, or Firm* — Abelman, Frayne & Schwab (57) ABSTRACT

This invention provides a method of ranking a characteristic of a liquid sample by providing a test container [11] having a viewing port [16] to liquid contained therein and through which electronic image data of a defined body of liquid sample [20] in the container can be captured. This data is compared with an electronic data model containing comparison data with which the captured electronic image data can be compared to provide a ranking. The image is captured and the image data is electronically compared with the comparison data to provide a characteristic ranking of the sample.

19 Claims, 7 Drawing Sheets

METHOD OF AND/OR APPARATUS FOR MONITORING A CHARACTERISTIC OF A LIQUID SAMPLE

CROSS REFERENCE TO RELATED APPLICATION

This application claims benefit under 35 U.S.C. § 371 to international application No. PCT/AU2014/050121, filed on Jul. 13, 2014, which claims priority to Australian application no. 2013902640, filed Jul. 16, 2013, the contents of which are incorporated by reference in their entireties.

TECHNICAL FIELD

This invention relates to a method of and/or apparatus for monitoring a characteristic of a liquid sample. This invention has particular but not exclusive application to monitoring a characteristic of a treated effluent sample which is indicative of the quality of the treated effluent and thus the efficiency of the plant from which it was discharged.

This invention may be utilisied for monitoring treated sewage for effective operation of on-site sewage treatment plants and particular reference will be made hereinafter to that application. However this invention may also be utilised for monitoring turbidity of liquid or of fluid mixtures which change opacity in a predictable manner with increase/decrease in the percentage of suspended particles in the liquid/fluid. This invention may also be utilised for monitoring water samples which, as worldwide population grow, presents a major problem for authorities tasked with maintaining the health of their citizens and their environment.

BACKGROUND ART

Many types of on-site sewage treatment plants are available which aim to continuously treat raw sewage and to discharge the treated effluent at a quality which can be safely and effectively discharged as a sub-soil discharge or as a surface discharge onto a dedicated soakage area. If effective treatment is not achieved, discharge of the treated effluent can cause hygiene problems, unpleasant odours, contamination of the environment and reduced cycle time between required periodical refurbishing of the on-site treatment plant and/or the discharge treatment.

While the problems associated with underperforming on-site sewage treatment plants is clear its solution is not, as it is not feasible to regularly dispatch trained personnel to test and monitor each on-site treatment plant for discharged effluent quality at a required standard. Furthermore assembling a meaningful database of information concerning the performance of on-site sewage treatment plants in a manner which may be readily used to assist decision-making in an attempt to improve a local environment is not currently practical.

Typically, discharged treated effluent is evaluated by measuring the percentage of total suspended solids (TSS) and/or biochemical oxygen demand (BOD) which is commonly measured over a five day period (BOD 5) and is widely used as a standard for evaluating a test sample. These tests, which require analysis in a laboratory, are expensive to conduct and take time to achieve a result which can be acted upon to rectify an underperforming treatment plant.

In an attempt to circumvent this problem, discharged treated effluent quality testing is often carried out by a trained analyst making a visual examination of the discharged treated effluent. This analyst based evaluation method is problematic since the test results are based on the analyst's skills. As a result there is no strict adherence to a standard and thus a treatment plant given a pass evaluation by one analyst may be rated as a fail evaluation by another analyst. Furthermore, the collection of data gathered by such methods does not provide an effective overview of the performance of on-site treatment plants in a given area on which sound decisions can be made with a view to improving the health of the populating citizen's environment. In addition, unscrupulous operators can easily provide incorrect information which may make gathered information unreliable.

This invention aims to provide a method of and/or apparatus for monitoring a characteristic of a liquid/fluid sample which will alleviate one or more of the disadvantages associated with the presently available methods, some of which are set out above.

SUMMARY OF INVENTION

With the foregoing in view, this invention in one aspect resides broadly in a method of monitoring a characteristic of a liquid sample including:
  providing a test container having a viewing port to liquid contained therein and through which electronic image data of a defined body of liquid sample in the container can be captured;
  providing an electronic data model containing comparison data with which the captured electronic image data can be compared to provide a ranking;
  capturing an image of the defined body of liquid sample in the container, and
  electronically comparing the captured image data with the comparison data to provide a characteristic ranking of the sample.

The characteristic is preferably the opacity of the liquid sample obtained by comparing image data captured through the liquid sample with image data captured through the empty test container. The image data may be computed from these electronic images using measures such as pixel density or count, greyscale value, spatial information or a contrast measurement such as of a target image viewed through the defined body of liquid and having contrasting colours. Opacity is preferred as a characteristic as tests have shown a relationship between TSS and opacity which can be represented by an algorithm which may be analysed to compare captured data and to provide a test TSS and which can be effectively modeled in the range of interest for testing outflows from on-site sewage treatment plants where results for total suspended solids in the liquid in the range of between 5 mg/liter and 50 mg/liter provides a suitable range for evaluating the effectiveness of the plant.

The electronic image may be taken by any suitable electronic camera. Preferably however the electronic camera incorporates wireless ability for communicating with a remote local station or via the Internet to a database held by a government authority for example whereby the image data may be transmitted to a remote database.

The characteristic could also be a measurement of light intensity of an electronic image held or downloaded from a camera which allows the user to manually set its parameters such as focal length, focus, aperture, and shutter speed to specified reference values whereby comparative light intensity measurements may provide the monitored characteristic.

In order to enhance the accuracy of the characteristic monitored it is preferred that a first electronic image be taken with a clean empty test container so that the "empty" electronic image may be compared to the comparison data held in the data model to establish a reference point from which the incremental change in the monitored characteristic for the test sample is computed and to maintain consistency of monitored characteristics from a wide range of test samples and to provide a method in which accuracy of results is not dependant on ambient light intensity. This method also aims to accommodate variations in image intensity from different cameras.

The data model may be maintained in a central database which may include a table of authorised users having cameras which may log into the central database to download the electronic image of a test sample to provide an image which may be analysed by the centralised database to obtain the characteristic assessment of the sample.

Preferably however the data model is held within the communications device of an authorized user whereby the characteristic assessment is computed by the communications device so as to provide the authorised user with the results of the characteristic assessment, enabling if necessary, adjustment of the on-site treatment plant immediately or in a timely manner after the test is performed. When effective operation of the on-site sewage treatment plant is achieved, further sample tests may be performed and transmitted to the centralised database, along with, if desired, information concerning the changes which were made to the treatment plant.

It is also preferred that the communication device be of the type having a OPS facility which preferably is automatically interrogated by the stored data model to record the GPS identified position of the test. Date and time data may also be recorded. However these functions may be optional functions and other identifying means may be utilised to identify the on-site treatment plant being tested.

The test information assessed by the data model is preferably utilised to build up a database for a respective login which may be held jointly or individually by the person conducting the test and/or the authority which monitors and/or regulates the operation of such on-site treatment plants. Such gathering of test information by an authority will provide a database which may be studied for improving the efficiency of the overall management of the on-site treatment plants, for highlighting deficiencies in a particular site or zone, or where the type of plant is recorded, the suitability or efficiency of a type or brand of on-site treatment plant in a particular area.

In a preferred embodiment of the invention a smart phone or other portable electronic communication device such as a tablet is utilised as the communication device and for capturing the electronic image data.

In a further aspect this invention resides broadly in a method of ranking the TSS of a turbid liquid sample, including:
  providing a test container for a sample to be tested whereby an opacity characteristic of the monitored sample may be obtained to provide an opacity ranking;
  obtaining an opacity ranking for the turbid liquid sample in the test container;
  providing an electronic data model able to provide a TSS ranking from an opacity ranking;
  electronically comparing the opacity ranking with the data, model to provide a TSS ranking of the sample;
  communicating the TSS ranking and/or the opacity ranking of the sample to a remote database via a portable communication device, whereby a record of indicative TSS values of the test samples may be monitored.

The turbid liquid sample may be a treated effluent sample obtained from an on-site sewage treatment plant and the opacity characteristic may be monitored utilising electronic image data retrieved from a defined body of liquid in the test container. The opacity characteristic may also be obtained from a test container having a light source which shines through the effluent sample in the test container as well as a luminance meter which comparatively measures incident light after passage through the sample. The opacity characteristic may also be a measure of the light reflection from the surface of a test sample if such reflection varies predictably with the percentage of total suspended substances in a sample liquid or a measure of the deflection or scattering of a directional light beam emitted from the light shone through the defined body of sample liquid.

In yet a further aspect this invention resides broadly in a method of establishing a database containing performance criteria of a plurality of on-site sewage treatment plants, the method including:
  providing a database with which an authorised operator may communicate using a mobile communications device capable of storing image data obtained from an electronic camera;
  causing each authorised operator to have a test container provided with a viewing port to a collected treated effluent sample contained therein and through which port desired electronic image test data of the treated effluent sample can be captured, and
  causing the authorised operator or operators to regularly obtain electronic image test data of treated effluent samples discharged from the on-site treatment plants and to communicate the test data obtained from each of the plurality of on-site treatment plants to the database so as to assemble data containing a record of a performance criteria of the plurality of on-site treatment plants.

Preferably the performance criteria is the quality of the treated effluent in terms of total suspended solids/substances as represented by the characteristic assessment data obtained from the electronic image of a sample of the treated effluent discharged from the primary treatment apparatus, such as an on-site sewage treatment system or home sewage treatment plant.

It is also preferred that the image be captured by a smart phone or other portable electronic device having similar functions for capturing images and for transmitting captured image data via the internet to a designated internet site as well as a GPS facility, and hereinafter collectively referred to as a smart phone, whereby information transmitted to the database contained on the designated internet site includes information concerning the time and date of the test and its GPS location. It is further preferred that the data model be available in the form of an app which can be downloaded to a smart phone.

An authorised person could be any selected person the authority controlling the database permits or authorises to communicate collected assessment data from on-site treatment plants. Alternatively an authorised person could be anyone the authority controlling the database provides the app to.

This method could also be used to establish a database containing assessment data of other liquid bodies wherein the total suspended solids in the liquid provide a criteria which is desired to be monitored by an authority.

In another aspect this invention resides broadly in a test container assembly for collecting a defined body of sample liquid, including:

a container having an open top through which sample liquid may be introduced into the container;

a feature on or associated with a wall of the container assembly;

a viewing port formed in the container assembly through which an electronic image may be taken of the feature both when the container is empty and when containing a defined sample of liquid containing suspended solids, and support means for supporting the lens of a camera aligned with the viewing port and at a fixed distance from the feature.

The container may be an opaque container requiring, illumination of the feature. Preferably however the container is a translucent or transparent container which admits sufficient ambient light to the marking to enable the desired electronic images of the feature to be captured through a collected sample. The feature may be the base wall of the container or a marking or pattern on or viewable through the base wall.

It is also preferred that, for consistency of results, the viewing port and the support means be formed so as to support a smart phone in a position with its camera lens aligned with the viewing port. This consistency will be achieved as a result of the restricted physical format of smart phones which necessarily are relatively thin and provided with substantially flat front and rear faces for support in a user's pocket or the like and which results in the camera lens being disposed at or closely adjacent to the substantially flat rear face of the smart phone and on which the camera may be readily supported in a stable manner. Additionally, effective alignment of the camera with the feature is readily monitored by reference to the image to be taken being displayed on the screen at the front face of the smart phone.

Thus in a very simple form the container assembly may be an open topped transparent container which may be rested upon a target marking in which a designated depth of sample liquid may be contained and having an open top against which the rear face of a smart phone may be rested to enable the lens to be operatively aligned with the target marking. Preferably however the marking is formed on the base wall and a cap is provided with a viewing port formed as a restricted opening spaced above the designated depth of the sample liquid. This arrangement will facilitate prevention of contamination of the smart phone by sample liquid in the container. This is important due to the potential proximity of the smart phone and a users mouth. The designated depth of sample liquid in the container may be provided by a marking in the container or by an overflow port at the designated depth.

Alternatively the marking could be formed in a sidewall of a rectangular container with the opposite sidewall providing the support for a smart phone and wherein the opposite sidewall forms the viewing port. A preferred form of marking is a Secchi Disc which provides clear delineation between equal components of black and the white segments as this facilitates comparative measurements such as changes in contrast and greyscale measurements.

A test container for monitoring by an electronic imaging device suitably allows sufficient ambient light to enter the container whereby the light intensity within the container is sufficient to enable an image to be recorded of the defined container contents without triggering the flash function of the camera. For this purpose the container may contain transparent or translucent sections. Alternatively the container may contain a powered light source. Where the viewing port is below the liquid level it should be formed of a translucent material which enables an image to be captured through the sample without reflection from the viewing port.

The defined body for sample liquid to be tested may be a container in which a set depth of liquid may be contained and in such embodiment the viewing port may be an aperture or non-reflecting lens in a top closure for the container. This set depth may be defined by a marking, or by providing a discharge port at the upper level of the set depth to prevent overfilling of the container. This provides a fixed parameter for reliably monitoring the desired characteristic for the test liquid and thus provide good accuracy and repeatability of results.

In yet a further aspect, this invention resides broadly in a method of on-site evaluation of treated effluent for an indication of the total suspended solids in the sample, including:

obtaining a treated effluent sample in a test container associated with a feature on which the camera in a smart phone supported by the open end of the container may focus;

loading the smart phone with a data model able to compare new image data with corresponding image data obtained from or based on evaluation of a plurality of test samples of known total suspended solids in the range of interest;

operatively supporting a smart camera on the open end of a test container and taking a photo of the feature through the sample in the container with the smart phone arranged in an operational mode which compares the new captured image data with the data model to establish a ranking representative of the total suspended solids of the sample, and displaying the ranking on the smart phone.

The smart phone may be supported directly on the open end of the test container or on a support which at least partially closes the open end and provides a viewing port for the camera lens at a set distance above the base configuration on which the camera focuses.

In a further aspect this invention resides broadly in a data model for use in any one of the methods set out above, including an algorithm formulated upon information derived from electronic image characteristics of a series of images taken through a defined body of clear liquid containing known incremental increases substantially as set out herein.

BRIEF DESCRIPTION OF DRAWINGS

In order that this invention may be more readily understood and put into practical effect reference will now be made to the accompanying drawings which illustrate typical applications of the present invention and wherein.

DESCRIPTION OF EMBODIMENTS

Figures 1, 2:
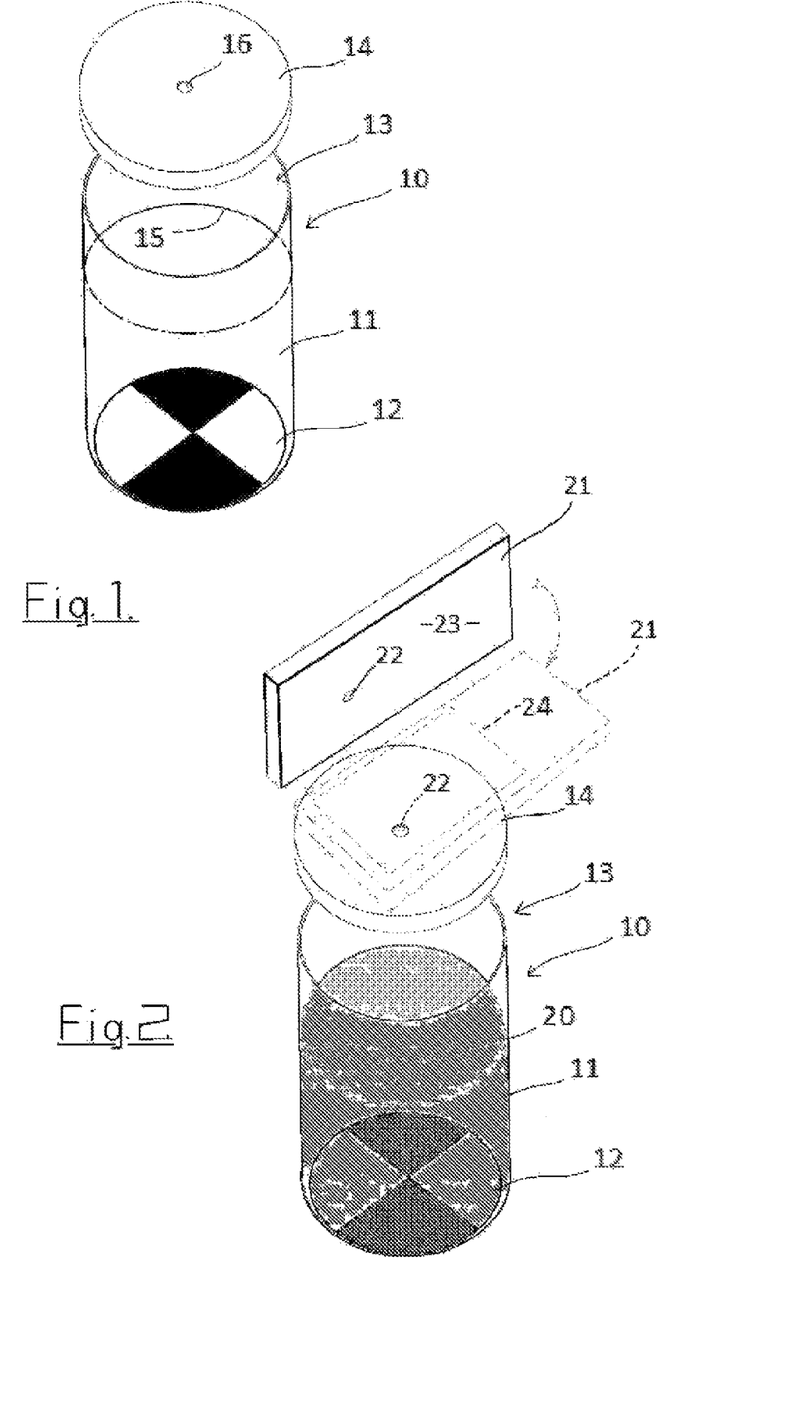
FIG. 1 is an exploded perspective view of one form of test container assembly according to this invention.
FIG. 2 is a further exploded view of the test container of FIG. 1 holding a test sample and a smart phone for capturing a test image.

FIG. 1 illustrates a test container assembly 10 which is formed as a transparent cylindrical glass container 11 having a Secchi Disc 12 on its base wall and an open top 13 which can be substantially closed by an apertured support lid 14. An internal inner circumferential moulding 15 is provided as a depth indicator for sample liquid such that when filled to that depth, a defined body of liquid sample is disposed above the Secchi Disc 12 and through which the electronic image data can be captured. A marking could also suffice. The aperture 16 in the support lid 14 is substantially coaxial with the Secchi Disc 12.

Figure 3:
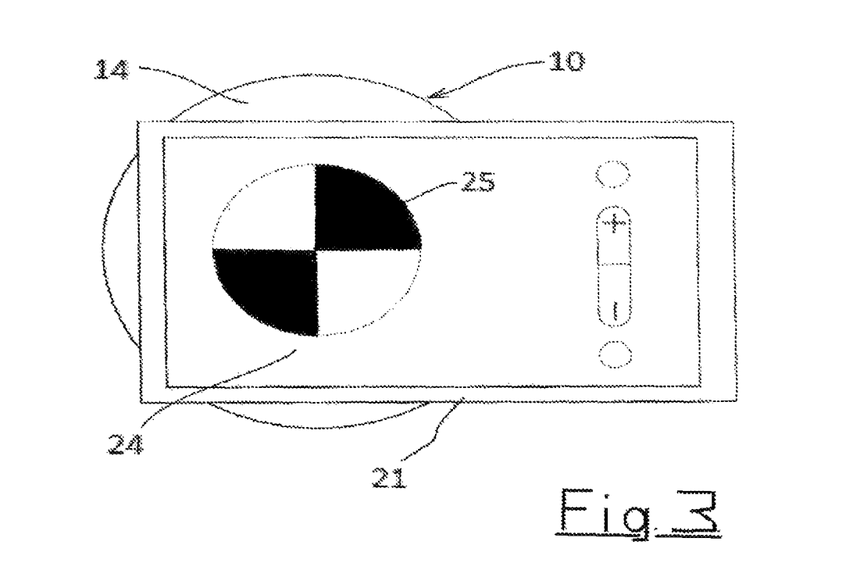
FIG. 3 is a plan view illustrating the smart phone and the camera image when supported by an empty test container.
Figure 4:
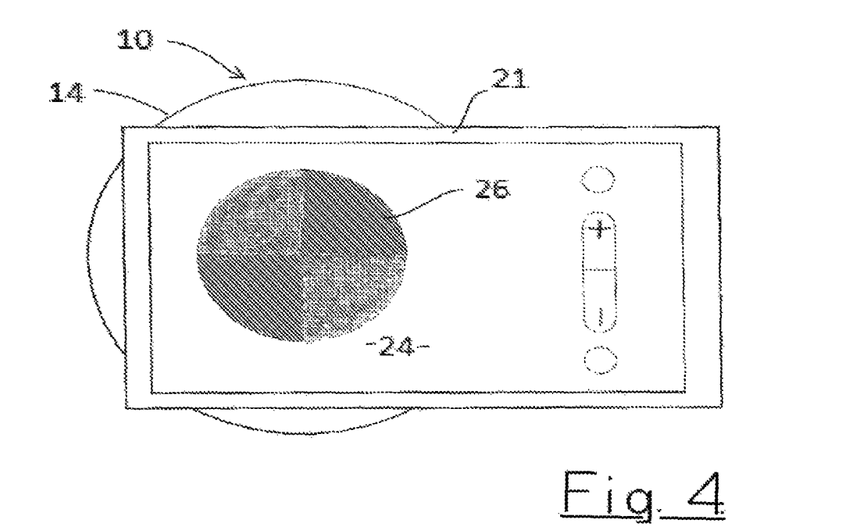
FIG. 4 is a view corresponding to FIG. 3 but illustrating the image obtained when a sample is introduced into the test container.

FIG. 2 illustrates the test container assembly 10 filled with a sample of treated effluent 20 to the level of the moulding 15. A smart phone 21 which has a viewport 22 for its camera disposed in the substantially planar back face 23 is also shown above the support lid 14. The camera 21 can be supported on its back face 23 on the upper flat face of the apertured lid 14 with its viewport 22 aligned with the aperture 16, as shown in dotted outline, so that the smart phone 21 is able to capture an image of the Secchi Disc 12, firstly as viewed through the empty transparent container 11 and subsequently as viewed through the sample liquid 20 which partially obscures the Secchi Disc 12, such that the contrast between the black and white zones is more fuzzy whereby an image of the disc 12 captured through the aperture 16 will be correspondingly fuzzy. Samples of the images obtained when the container 11 is empty and filled with a predetermined depth of treated sewage or other liquid containing suspended solids are shown in FIGS. 3 and 4 respectively. Each image is displayed on the screen 24 to provide a visible check of correct alignment between the phone 21 and the container assembly 10 and capture of the appropriate image.

The clear image 25 illustrated in FIG. 3 can be analysed for greyscale value, which in this image indicated an overall average % greyscale of 35% as may the fuzzy image 26 illustrated in FIG. 4, which indicated an overall average % greyscale of 56.9%. Similarly an algorithm or data model against which the % greyscale values of the test images 25 and 26 can be compared is compiled by first obtaining a series of greyscale values in the range of interest of samples with known starting and incremental changes in the amount of suspended solids contained in the sample so as to establish a greyscale model with which a test sample % greyscale can be compared to register an equivalent % value which is indicative of the total suspended solids in the test sample.

This data model along with other required information is suitably made the subject of an app which may be downloaded onto a smart phone so as to equip that smart phone for use in testing on-site sewage treatment plants for the quality of the treated effluent which is being discharged either subsoil or onto a dedicated soakage area. The app suitably contains a data model with which the captured electronic image data can be compared. The data model is suitably derived from test results conducted in the same manner as an infield operator to derive comparative image data which corresponds to known percentages of total suspended solids in a clear liquid.

Figure 5A:
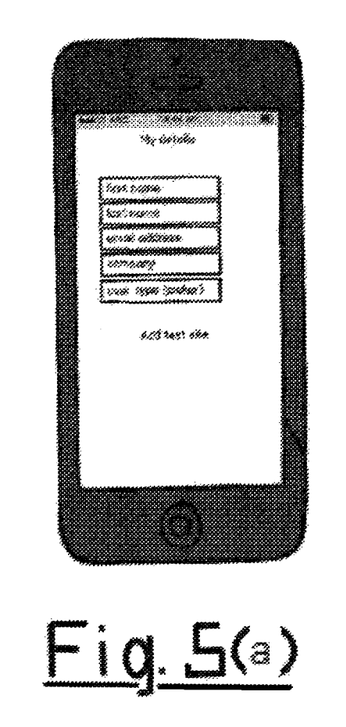
FIGS. 5(a) to 5(i) illustrate a series of smart phone views showing the recordal operation sequence.

FIGS. 5(a) to 5(i) are schematic views illustrating the screen information which appears on a smart phone screen 24 which has downloaded the preferred app and which is used to conduct a test of the outflow from an on-site sewage treatment plant. FIG. 5(a) is the screen which appears after an operator has approached an authority to be licensed and suitably has received the appropriate test container assembly 12 and has downloaded the app onto their smart phone. This screen provides prompts for the new certified operator to enter their details. Once entered, the information will be communicated to the authority to check the veracity of the details. The prompts include a "user type" prompt which when selected provides a list of the types of operators that may be authorised by the authority to conduct quality tests of treated sewage.

Figure 5B:
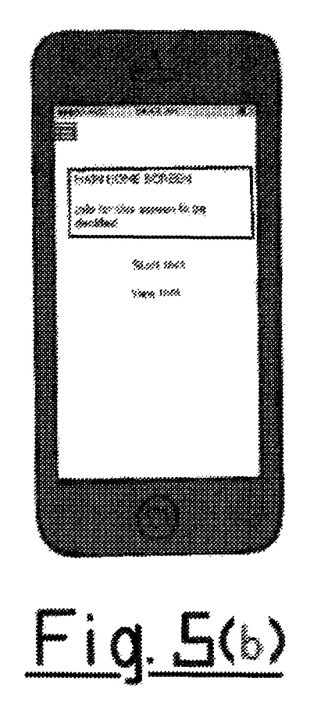
Figure 5C:
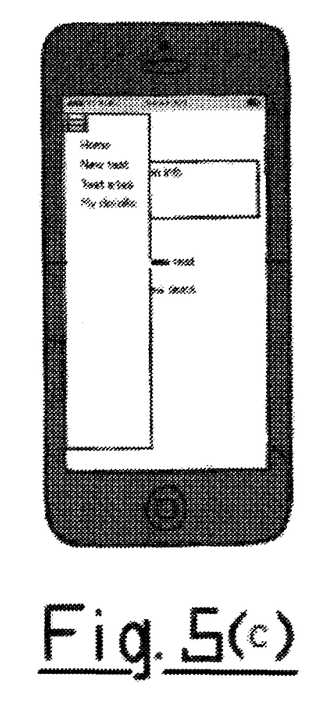

The "Home Screen" is illustrated in FIG. 5(b) and provides prompts for "start test" and "view test". FIG. 5(c) illustrates the home screen with a pop-up section with prompts for entering details of the on-site treatment plant being monitored. As information is entered an ordered list of near monitored on-site treatment plants is shown from which the appropriate site can be selected as illustrated in FIG. 5(g). If the site is a new site which is not listed, the screen will switch to that illustrated in FIG. 5(f) which brings a local map image and prompts for entering the new address, the property owners name and service interval.

Figure 5D:
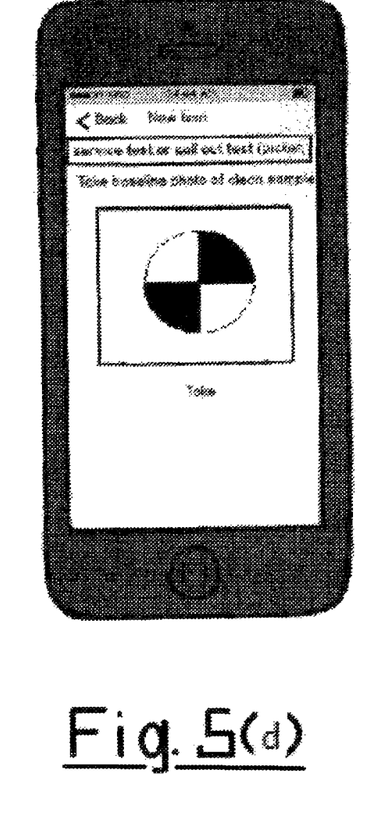
Figure 5E:
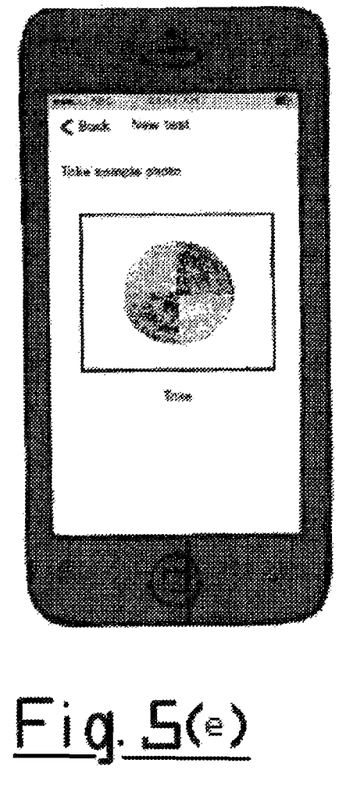
Figure 5F:
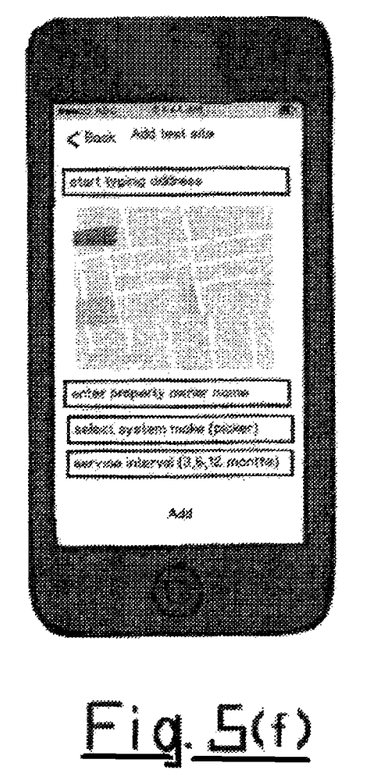
Figure 5G:
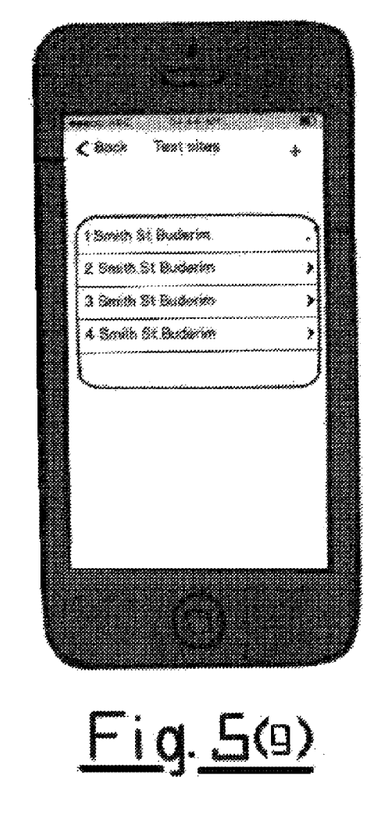
Figure 5H:
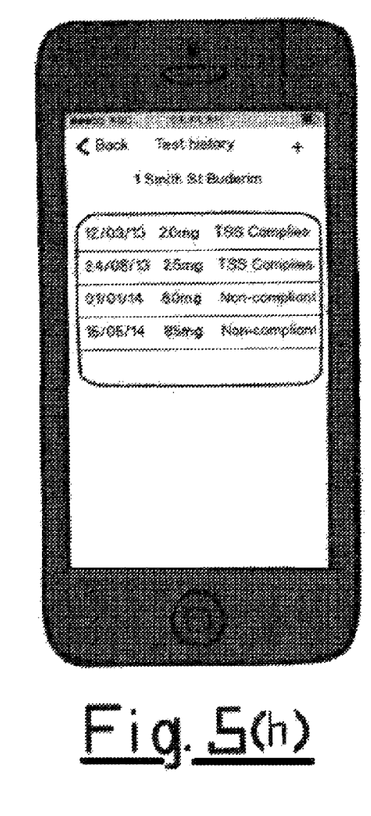
Figure 5I:
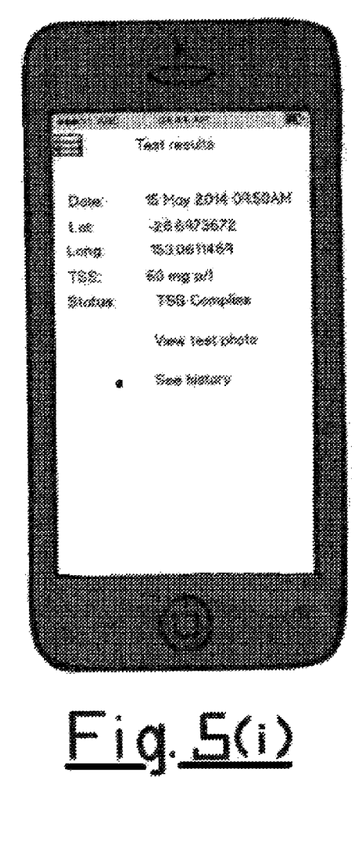

After the site has been selected or entered and the "new test" prompt is selected, the display illustrated in FIG. 5(d) appears prompting the operator to take a baseline photograph of the Secchi Disc image 12 with their smart phone 16. This image will appear on the screen 24 as illustrated in FIG. 5 (d) providing confirmation that the camera is correctly aligned with the test container assembly 10 and additionally it provides a reference point for the data model to calculate the incremental change when the sample image is taken as illustrated in FIG. 5(e) through the sample illustrated in FIG. 2 filled to the reference level 15. After the results have been calculated the screen illustrated in FIG. 5(i) appears showing the results in terms of total suspended solids as well as providing a date reference and a GPS position. This view also indicates whether or not the tested on-site treatment plant is compliant or non-compliant with the standards set by the authority.

Both photographs are used in the comparison, as the % greyscale will vary with ambient light conditions and utilising both images provides a reference since the "zero" point corresponding to the image in FIG. 3 can be referenced to a corresponding value in the data model. The operator can select the "test results" from the screen illustrated in FIG. 5(i) and the screen illustrated in FIG. 5(h) will display the test address and results from previous tests. If the results are dated subsequent to the required test interval date, an overdue prompt will appear.

Should the test be indicated as non-compliant, the operator may take immediate steps to rectify problems with the on-site treatment plant and re-submit tests to show that changes made to the plant have bought it up to standard. In addition the authority's database will contain a historical record of the tests conducted on all their sites and suitably indicating the type as well as brand of on-site treatment plant such that any underperforming type or a respective underperforming plant can be improved to meet the required standard or made non-compliant.

Figure 6:
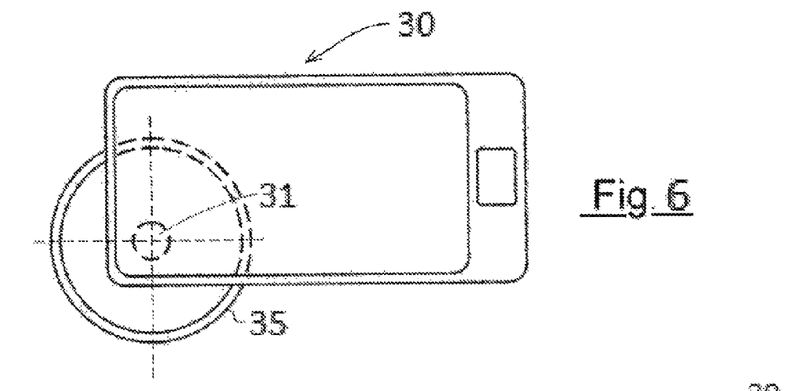
FIG. 6 is a view similar to FIG. 3 but illustrating a different smart phone positioned above the test container.
Figure 7:
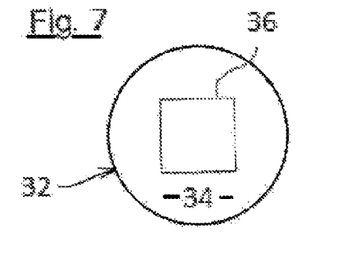
FIG. 7 is a plan view of an alternate form of test container.
Figure 8:
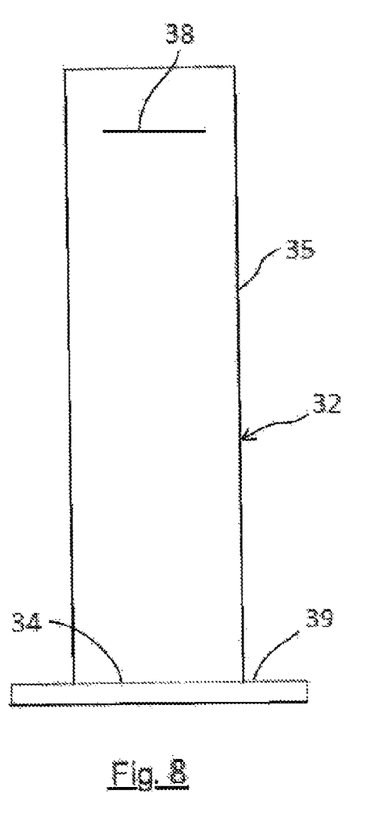
FIG. 8 is a side view of the test container of FIG. 7.
Figure 9:
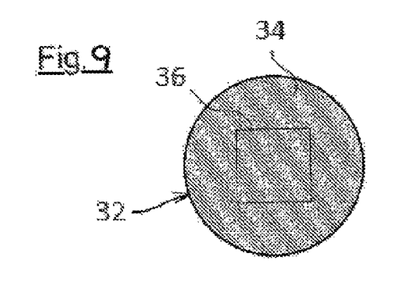
FIG. 9 is a plan view of the test container of FIG. 7 containing a test sample.
Figure 10:
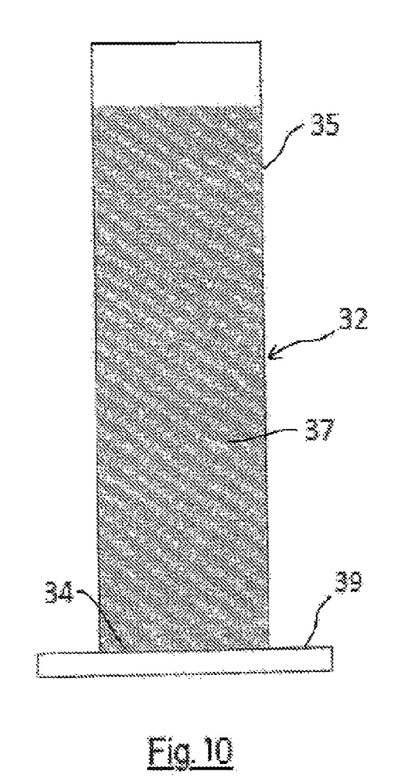
FIG. 10 is a side view of the test container of FIG. 7 containing a sample.

FIG. 6 illustrates a smart phone 30 provided with a viewport 31 adjacent a corner thereof such that the smart phone 30 is supported asymmetrically with respect to the test container assembly 32 to capture the required image. Additionally as illustrated in FIGS. 7 to 10 the test container assembly 32 has a base wall 34 which extends outwardly from the tubular transparent body 35 and the feature 36 on the internal face of the base wall is a square. In this embodiment level of the test sample 37 is indicated by a marker 38 on the transparent tubular body 35.

Figure 11:
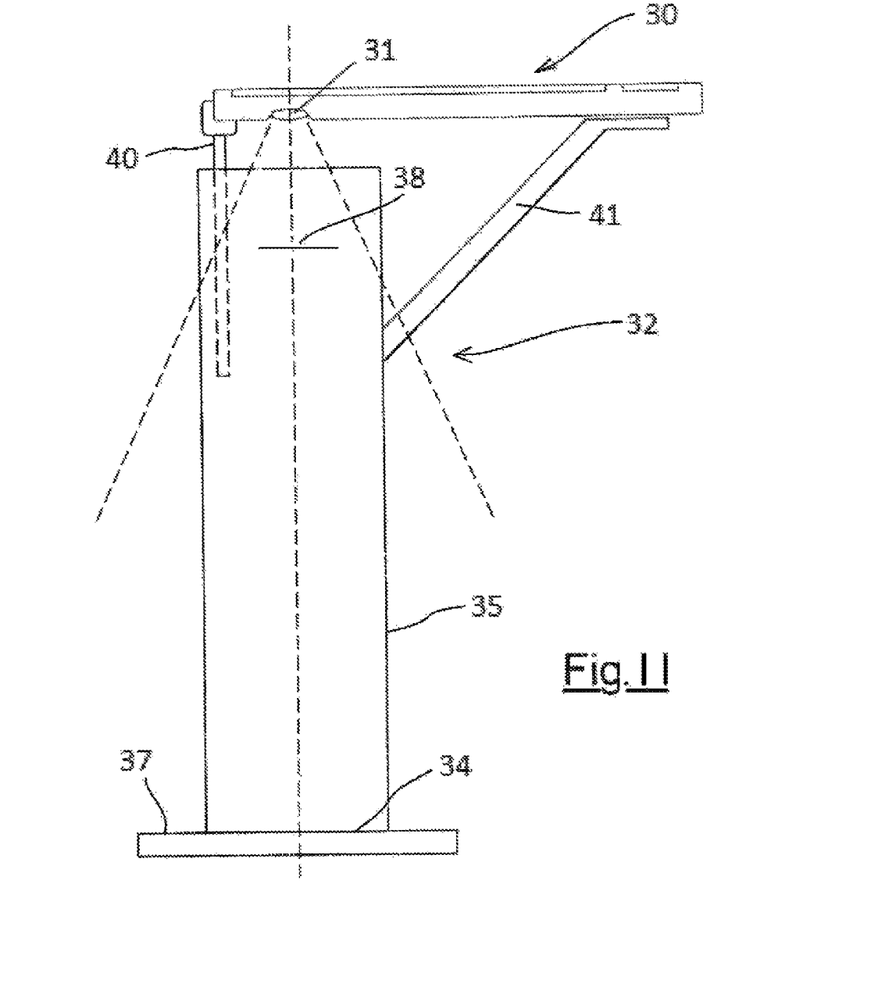
FIG. 11 illustrates the configuration of the support means for a smart phone arranged for capturing the test image contained in the test container of FIGS. 7 to 10.

The portion of the base wall 34 extending outwardly from the transparent body provides a white band 39 surrounding the internal base wall, the image of which is intended for capture by a smart phone 30. This ensures that image results will not be affected by the surface on which the test container assembly 32 is supported. In any event the portion of the image taken for analysing can be selected by the data model and may not include the full area of the image. In this embodiment the smart phone 30 is supported elevated above the test container assembly 32 by an internal leg 40 and an inclined support 41 for the overhanging portion of the phone 30 as illustrated in FIG. 11.

In use, an operator wanting to check the quality of treated effluent firstly obtains an image of the base wall of the test container assembly 10 or 32 by placing the lid 14 or other phone support structure on the open top of the empty container 11 or 35 and the viewport of a smart phone loaded with the appropriate data model is rested upon the lid 14 or other phone support structure with its viewport 22 or 31 positioned to capture an image of the base wall. This image will be indicated on the phone screen prior to taking the necessary photograph.

This operation is repeated with the test container assembly 10 or 32 filled to the indicated level with a sample of the effluent or dirty water to be tested. In both empty and filled instances the viewport 22 or 31 will be positioned at the same distance from the base wall for the image of the base wall of the empty container and the image of the base wall for the filled container.

This ensures that the characteristic variations, such as in greyscale or pixel counts or the like, will result overwhelmingly from the nature of the sample liquid in the container and particularly the total suspended solids contained in the liquor. This incremental change is analysed by the data model to provide an indication of the total percentage of suspended solids in the liquor.

Apart from ensuring that the sample liquid is filled to the appropriate depth, all results are outside the control of the operator. By gathering all the data in a central database an operator who consistently provides false readings could be revealed by suitable audits of on-site plants to reveal any pattern of irregularity.

It will thus be seen that in a situation where consistency of test results based on electronic images of a sample are required to achieve uniform rating of operating systems from inputs by a multitude of operators and or stations, the recognition that the use of smart phones with their camera lens juxtaposed to the flat back wall on which each smart phone may be simply supported and positioned to capture the necessary image provides unexpected advantages by simply maintaining each camera lens substantially at the same distance from the test sample within only small and insignificant variations likely to occur.

It will also be seen that utilising readily available cameras to obtain test results and to communicate those results via the Internet to a central database provides a hitherto unavailable real time collection of data which may be compared, for example, with ambient weather conditions or other criteria at the time of the test to provide a useful database which may be used to streamline and improve the operation of on-site sewage treatment plants with attendant benefits to the community and to the environment.

It will of course be realised that the above has been given by way of illustrated example of aspects of this invention and that all modifications and variations thereto as would be apparent to persons skilled in the art are deemed to fall within the broad scope and ambit of this invention as is defined in the appended claims.

I claim:

1. A method of ranking a characteristic of a liquid sample including:
    providing a test container having a viewing port to liquid contained therein and through which electronic image data of a defined body of liquid sample in the container can be captured;
    providing an electronic data model containing comparison data with which the captured electronic image data can be compared to provide a ranking;
    capturing an image of the defined body of liquid sample in the container, and electronically comparing the captured image data with the comparison data to provide a characteristic ranking of the sample.

2. The method of claim 1, wherein the characteristic is the opacity of the liquid obtained by comparing image data captured through the liquid sample with the electronic data model.

3. The method of claim 1, wherein the electronic data model compares a captured image data with corresponding image data obtained from or based on evaluation of a plurality of test samples of known quality in the range in respect of which a ranking is required.

4. The method of claim 3, wherein the evaluated known quality is a measure of the total suspended solids in the liquid and wherein the range of interest is between Sing/liter and 50 mg/liter, whereby the characteristic ranking is a ranking of the total suspended solids in the sample.

5. The method of claim 1, wherein the electronic image data is captured by a camera of a smart phone and wherein the electronic data model is loaded onto the smart phone.

6. The method of claim 5, wherein electronic image data captured by the smart phone or the characteristic ranking provided by the data model is transmitted to a remote database base which maintains records for a geographical area.

7. The method of claim 6, wherein the smart phone has a GPS facility and wherein the data model includes a function which establishes the GPS location at which the test image is taken and includes that information in data transmitted to the remote database.

8. A method of establishing a database containing performance criteria of a plurality of on-site sewage treatment plants, the method including;
    providing a database with which an authorized operator may communicate using a mobile communications device capable of storing image data obtained from an electronic cam era;
    causing each authorized operator to have a test container provided with a viewing port to a collected treated effluent sample contained therein and through which port desired electronic image test data of the treated effluent sample can be captured, and
    causing the authorized operator or operators to regularly obtain electronic image test data of treated effluent samples discharged from the on-site treatment plants and to communicate the test data obtained from each of the plurality of on-site treatment plants to the database so as to assemble a data containing a record of a performance criteria of the plurality of on-site treatment plants.

9. The method of claim 8 further including;
providing the mobile communications device with an electronic data model containing comparison data with which the captured electronic image test data can be compared to provide a ranking;
comparing the electronic image test data with the comparison data to provide a ranking for the test sample, and
displaying the ranking on the mobile communications device.

10. The method of claim 8, wherein the electronic test data is a measure of the opacity of a test sample and wherein the test container is formed to hold a predetermined depth of fluid above a feature on which an electronic camera may focus both when the container is empty and when the container contains a test sample of a collected treated effluent sample.

11. The method of claim 8, wherein the mobile communications device is a smart phone having a GPS facility, the method further including causing the smart phone to transmit information concerning the time and date of the test and its GPS location to the databases together with the test data.

12. The method of claim 11, wherein the smart phone is loaded with the data model downloaded in the form of an app.

13. A method of on-site evaluation of treated effluent for an indication of the total suspended solids in the sample, including:
obtaining a treated effluent sample in a test container associated with a feature on which the camera in a smart phone supported by the open end of the container may focus;
loading the smart phone with a data model able to compare new image data with corresponding image data obtained from or based on evaluation of a plurality of test samples of known total suspended solids in the range of interest;
operatively supporting a smart camera on the open end of a test container and taking a photo of the feature through the sample in the container with the smart phone arranged in an operational mode which compares the new captured image data with the data model to establish a ranking representative of the total suspended solids of the sample, and
displaying the ranking on the smart phone.

14. The method of claim 13 including: providing a support which at least partially closes the open end of the test container and provides a viewing port for the camera lens at a set distance above the base configuration on which the camera focuses.

15. A test container assembly for collecting a defined body of sample liquid, including:
a container having an open top through which sample liquid may be introduced into the container;
a feature on or associated with a wall of the container assembly;
a viewing port formed in the container assembly through which an electronic image may be taken of the feature both when the container is empty and when containing a defined sample of liquid containing suspended solids, and
support means for supporting the lens of a camera aligned with the viewing port and at a fixed distance from the feature.

16. The method of claim 15, wherein the support means is a flat upper surface of an apertured lid which locates about the upper end of the container and through which the required image may be captured by a smart phone.

17. The method of claim 15, wherein the test container is a translucent container.

18. The test container of claim 15, wherein the feature is a marking or pattern on or viewable through the base wall of the test container.

19. The test container of claim 15, wherein the viewing port is formed as a restricted opening in an apertured lid spaced above the sample liquid.

\* \* \* \* \*